US005193745A

United States Patent [19]

Holm

[11] Patent Number: 5,193,745

[45] Date of Patent: Mar. 16, 1993

[54] ATOMIZING NOZZLE DEVICE FOR ATOMIZING A FLUID AND AN INHALER

[76] Inventor: Karl Holm, Hedevejen 8, Tranum 9460 Brovst, Denmark

[21] Appl. No.: 585,055

[22] PCT Filed: Mar. 7, 1990

[86] PCT No.: PCT/DK90/00063

§ 371 Date: Oct. 12, 1990

§ 102(e) Date: Oct. 12, 1990

[87] PCT Pub. No.: WO90/10469

PCT Pub. Date: Sep. 20, 1990

[30] Foreign Application Priority Data

Mar. 7, 1989 [DK] Denmark ............................ 1077/89

Mar. 17, 1989 [DK] Denmark ............................ 1295/89

[51] Int. Cl.[5] ........................ B05B 1/08; A61M 11/00

[52] U.S. Cl. ................................ 239/102.2; 137/554; 128/200.23

[58] Field of Search ..................... 239/102.2, 583-585; 137/554; 251/129.01; 128/200.23

[56] References Cited

U.S. PATENT DOCUMENTS 3,884,417 5/1975 Scheffield et al. .
3,949,938 4/1976 Goodinge .
3,993,247 11/1976 Tyler .................................. 137/554
4,000,852 1/1977 Martin .
4,033,507 7/1977 Frömel et al. .
4,043,351 8/1977 Durling ............................... 137/554
4,067,496 1/1978 Martin .
4,122,378 10/1978 Brown .
4,142,973 3/1979 Kachman ............................ 137/554
4,166,577 9/1979 Elwell .
4,183,467 1/1980 Sheraton et al. .................... 137/554
4,276,903 7/1981 Spohr ................................. 137/554
4,313,571 2/1982 Bellicardi et al. .
4,340,181 7/1982 Stumpp et al. .
4,341,241 7/1982 Baker ................................. 137/554
4,398,670 8/1983 Hoffmann .
4,537,353 8/1985 Speranza .
4,643,223 2/1987 Abe et al. ............................ 137/554
4,655,396 4/1987 Taxon et al. .
4,674,491 6/1987 Brugger et al. ................ 128/200.14
4,726,523 2/1988 Kokubo et al. .
4,739,929 4/1988 Brandner et al. .
4,784,178 11/1988 Kasaya et al. ...................... 137/554

FOREIGN PATENT DOCUMENTS 0202381 11/1986 European Pat. Off. .
617088 8/1935 Fed. Rep. of Germany .
2826214 12/1979 Fed. Rep. of Germany ...... 137/554
WO86/05722 10/1986 PCT Int'l Appl. .
WO87/04354 7/1987 PCT Int'l Appl. .

OTHER PUBLICATIONS

"Operating Characteristics of a Vibrating-Type Atomizing Nozzle" by Sliepcevich, Consiglio & Kurata.

*Primary Examiner*—Andres Kashnikow
*Assistant Examiner*—Lesley D. Morris
*Attorney, Agent, or Firm*—Merchant, Gould, Smith, Edell, Welter & Schmidt

[57] ABSTRACT

An atomizing nozzle device comprises a housing in which an inner chamber is defined. Fluid is introduced into the chamber and is discharged therefrom through an orifice of a metallic screw cap of the device. Within the chamber a stem is arranged, which stem is connected to a closing head cooperating with the orifice through a rod. A spring acts on the stem for causing the head to close the orifice and consequently prevent the discharge of fluid from the device. A solenoid coil is provided and supplied with a current through a current path in which a switch contact is established through the cooperating closing head and the end cap. By the supply of an energizing current to the solenoid coil, the stem is caused to move causing the closing head to move relative to the orifice for opening the orifice and consequently discharging fluid from the nozzle device. By the movement of the closing head relative to the cap, the current supply to the solenoid coil is interrupted resulting in that the spring forces the closing head to close the orifice. Through the establishment and interruption of the current path to the solenoid coil, a self-controlled vibrating-type nozzle device is provided.

34 Claims, 4 Drawing Sheets

ATOMIZING NOZZLE DEVICE FOR ATOMIZING A FLUID AND AN INHALER

Figure 1:
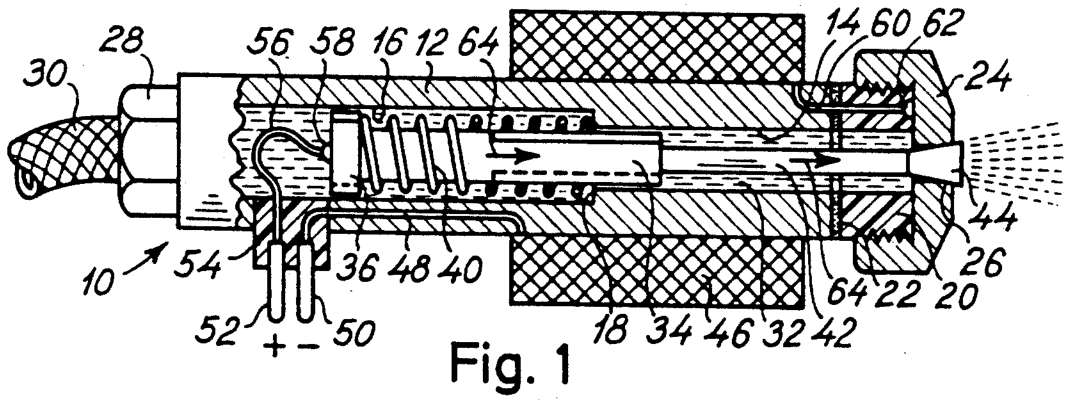

The present invention relates to the technical field of atomizing a fluid, such as a liquid. The present invention more specifically relates to an atomizing nozzle device for atomizing a fluid supplied thereto. The fluid may constitute a liquid or a gas, which is supplied to the atomizing nozzle device at an elevated pressure as compared to the atmospheric pressure or any other pressure prevailing in an environment, in which the atomizing nozzle device is operated. The elevated pressure may for most applications constitute a superatmospheric pressure for most applications less than 10 ato. The fluid to be atomized by means of the atomizing nozzle device may as indicated above, constitute a gas or a liquid. The liquid may be e.g. water or an aqueous solution to be discharged or injected, e.g. in a fire extinguishing system or the like, or may be a combustible liquid such as petrol, gasoline, diesel or any other combustible gas injected into a combustion chamber, e.g. a combustion chamber of a combustion engine. A particular application of the present invention is within the therapeutical field, according to which application, an inhaler is provided comprising an atomizing nozzle device for atomizing the fluid or liquid comprising a drug to be inhaled by a patient.

In numerous references, the technique of injecting a liquid into e.g. a combustion chamber or into a gaseous medium is described. Reference is made to U.S. Pat. Nos. 4.313,571, 3,884,417, 4,000,852, 4,033,507, 4,166,577, 4,398,670. 4,726,523 and 4,739,929, which references are herewith incorporated in the present specification by reference. Numerous of these references describe pressure controlled injection valves or nozzles in which the discharging and atomizing of the fluid, such as the combustible fluid which is supplied to the valve, is controlled by the pressure of the fluid supplied to the valve or nozzle. These pressure controlled atomizing nozzles have been refined and have even been elaborated by providing a feedback signal indicating whether the fuel is discharged from the valve or not.

Thus, U.S. Pat. No. 4,398,670 discloses a fuel injection valve for an internal combustion engine, in which valve a set of contact elements for generating an on/off signal representing the on/off states of the valve is provided. Still, this known fuel injection valve is an atomizing nozzle device, the operation of which is totally controlled by the input pressure of the fuel supplied to the valve and the discharge of the fuel from which is controlled by the input pressure.

In an article in Industrial and Engineering Chemistry. Vol. 42. No 11, pages 2353–2358, Nov. 1950 by C. M. Sliepcevich. J. A. Consiglio and Fred Kurata, University of Michigan, Ann Arbor, Mich., *Operating Characteristics of a Vibrating-Type Atomizing Nozzle,* the vibrating-type atomizing nozzle in discussed in greater detail. In the article, the vibrating-type atomizing nozzle is compared to a "conventional" atomizing nozzle, i.e. a nozzle comprising a simple orifice, from which the liquid is discharged. It is evident from the article that a vibrating-type atomizing nozzle is capable of generating a far more refined jet of droplets and droplets of a smaller diameter than an atomizing nozzle, in which the atomizing is simply carried out by means of a discharge orifice.

An object of the present invention is to provide an improved vibrating-type atomizing nozzle, which renders it possible to provide a jet of extremely small droplets, i.e. droplets of a diameter of $0.5 \propto 5$ μm, which atomizing nozzle device further renders it possible to control the discharging of the fluid from the atomizing nozzle device as pulsed, discharged jets with a substantially constant diameter of the droplets irrespective of the pressure of the fluid supplied to the atomizing nozzle device.

A further object of the present invention is to provide an atomizing nozzle device, the discharge of fluid from which is independent to any substantial extent of any fluctuations in the pressure prevailing in the fluid supplied to the atomizing nozzle device.

A still further object of the present invention is to provide an atomizing nozzle device of the vibrating-type, which in a closed loop control mode generates a jet of droplets of a diameter smaller than a comparable atomizing nozzle device of any known structure and of the pressure controlled type.

A still further object of the present invention is to provide an atomizing nozzle device of a simple structure which may easily be manufactured from a minimum of components and which provides a highly reliable vibrating-type nozzle device, which atomizing nozzle device is easily controllable, may be operated reliably for an extremely long period of time and is to an extremely small extent susceptible to wear and changes of operation characteristics due to wear of vital components of the atomizing nozzle device.

These and other objects and further numerous advantages and features characteristic of the present invention are obtained by an atomizing nozzle device according to the present invention for atomizing a fluid supplied thereto and comprising:

a housing having an outer wall defining an inner chamber of said housing, an inlet for introducing said fluid into said chamber, and an orifice for discharging said fluid from said chamber, a stem means comprising a closing element, said stem means being arranged within said housing so as to arrange said closing element juxtaposed said orifice for cooperating therewith, a spring means acting on said stem means for forcing said closing element thereof into said orifice for closing said orifice, an electro-mechanical driver means comprising a movable component and a stationary component, said movable component being connected to said stem means and said stationary component being connected to said housing, and said electro-mechanical drive means comprising connector means for receiving an electrical signal for causing said movable component to move relative to said stationary component and furthermore causing said closing element of said stem means to move relative to said orifice for opening said orifice and a switch means including a first switch component and a second switch component, said first switch component being connected to said stem means and being movable therewith, said second switch component being connected to said stationary component, said first and second switch components being in contact with one another and establishing a current path to said connector means when said orifice is closed by said closing element, and said first and second switch components being out of contact with one another and interrupting said current path when said closing element is moved relative to said orifice.

By the provision of an integral switch means of the atomizing nozzle device according to the present invention, a very simple, yet reliable, control loop is established. This control loop simply activates/deactivates the electro-mechanical driver means in response to the position and movement of the stem means, which further controls the discharging of the atomized fluid from the atomizing nozzle device by the opening of the orifice by means of the closing element. It is to be realised that the operation of the atomizing nozzle device according to the present invention depends on a simple on/off switching means and a spring loaded stem means and further that the discharge of fluid from the atomizing nozzle device is determined exclusively by the signal supplied to the electro-mechanical driver means and the characteristics of the component of the atomizing nozzle device, such as the characteristics of the spring means, and the dimensions of the orifice and the closing element. The operation of the atomizing nozzle device in its closed loop on/off mode is to a substantial extent independent of the pressure of the fluid supplied to the atomizing nozzle device or at least independent of fluctuations or variations of the supplied pressure.

It is believed that the teachings of the present invention providing a control loop within an atomizing nozzle device, which control loop controls the dimensions of the droplets generated by the atomizing nozzle device renders it possible to refine the vibrating-type atomizing nozzle so that a vibrating-type atomizing nozzle may be provided in accordance with the teachings of the present invention, which vibrating-type atomizing nozzle is capable of generating a far more refined jet of droplets and droplets of a smaller diameter than a known pressure controlled vibrating-type atomizing nozzle such as the nozzle of the type disclosed above in the above references and in the above article.

The switch means including the first switch component and the second switch component characteristic of the present invention may be constituted by separate switch components arranged in the atomizing nozzle device in any appropriate manner, e.g. separated from the inner chamber of the housing for eliminating any contact between the switch means and the fluid supplied to the inner chamber of the atomizing nozzle device. As will be discussed in greater detail below, by providing the switch means separated from the inner chamber to which the fluid to be atomized by the atomizing nozzle device according to the present invention is supplied, any danger of causing a fire due to the generation of sparks by means of the switch means is eliminated.

The generation of sparks when the switch components of the switch means are brought into contact or out of contact with one another may, as will be described in greater detail below, be eliminated in a preferred embodiment of the atomizing nozzle device, in which preferred embodiment an electronic circuit reduces the current transmitted through the switch means of the atomizing nozzle device to an extremely low level, at which any risk of generating sparks is eliminated. Thus, in accordance with an extremely simple embodiment of the atomizing nozzle device according to the present invention, the switch means is constituted by cooperating, integral components of the atomizing nozzle device. Thus, in accordance with this embodiment of the atomizing nozzle device according to the present invention, the dosing element is made from a metallic material and the first switch component is constituted by the closing element. Similarly, the orifice is provided in a housing component of the housing, which housing component is made from a metallic component and constitutes the second switch component. In this embodiment of the atomizing nozzle device according to the present invention, the operation of the atomizing nozzle device is controlled by the fluid atomizing means of the atomizing nozzle device, viz, the orifice and the closing element, as the closing element and the orifice on the one hand by their characteristics determine the degree of atomization of the fluid discharged from the atomizing nozzle device and on the other hand establishes and interrupts the current path to the electro-mechanical driver means, which operates the stem means and consequently causes the closing element to move relative to the orifice.

The electro-mechanical driver means may in accordance with the teachings of the present invention be implemented in numerous ways, e.g in accordance with piezo-electric driver techniques, electro-static driver techniques, etc. In the presently preferred embodiments of the atomizing nozzle device according to the present invention, the electro-magnetic driver technique is, however, utilized. The electro-magnetic driver technique may be implemented in accordance with an electro-magnetic, alternatively an electro-dynamic, driver technique. Thus, in a first embodiment of the atomizing nozzle device according to the present invention, the electro-mechanical driver means is constituted by an electro-magnetic driver means comprising a magnetic assembly and a coil. The magnetic assembly defines a magnetic gap, in which the coil is arranged, the magnetic assembly constitutes the stationary component and the coil constitutes the movable component.

In an alternative embodiment, the electro-mechanical driver means is constituted by an electro-magnetic driver means comprising a magnetic assembly and coil. The magnetic assembly defines a magnetic gap in which the coil is arranged, the magnetic assembly constitutes the movable component, and the coil constitutes the stationary component.

In accordance with an alternative electro-magnetic embodiment, the electro-mechanical driver means comprises a coil and an armature, which coil constitutes the stationary component, and which armature constitutes the movable component. The armature may constitute a separate component connected to the stem means, however, in accordance with the presently preferred embodiment of the atomizing nozzle device according to the present invention, the armature is constituted by an iron component of the stem means.

The signal supplied to the electro-mechanical driver means for causing the movable component to move relative to the stationary component may be generated by an external signal generator, such as an external AC or DC power supply, an external signal generator or the like generating a voltage signal, a current signal or a combination thereof. In a preferred embodiment of the atomizing nozzle device according to the present invention, the signal supplied to the electro-mechanical driver means is generated by a signal generator means constituting a part or a component of the atomizing nozzle device according to the present invention.

As indicated above, the signal generator means may generate any appropriate signal in view of the particular requirements, such as an AC signal, e.g, a sinusoidal signal, a square wave signal, a triangularly shaped signal, or a DC signal, or alternatively any combination of an AC signal and a DC signal. It is to be emphasized that, as will be evident from the detailed description below, the signal may be employed for synchronizing the discharging of fluid from the atomizing nozzle device to a specific requirement, for discharging pulses of fluid from the atomizing nozzle device or for synchronizing the discharging of fluid from the atomizing nozzle device relative to an external function or operation, such as the operation of an engine or the like. The control signal generated by the signal generator means may constitute a pulse signal, which is superimposed the electro-mechanical driver means for enabling the operation of the atomizing nozzle device according to the present invention within an enabling time period determined by the signal generated by the signal generator means. Alternatively or furthermore, the signal generator means may be externally controllable and may be enabled from an external source, such as an external control device, e.g, an external control computer, for controlling the generation of the signal within the signal generator means, for modifying or altering the signal generated by the signal generator means in accordance with specific requirements, or for fulfilling a specific function.

It is believed that the atomizing nozzle device according to the prevent invention may be operated in its autonomously operating mode continuously or in an intermittent operational mode by the supply of an AC signal, such as an AC signal of a frequency of 0.01 Hz–10 kHz, to the electro-mechanical driver means. The closing element of the atomizing nozzle device may, dependent on the characteristics of the fluid in question and on the physical properties of the atomizing nozzle device, be operated within a frequency range of 10 Hz–5 kHz, preferably within the range of 50 Hz–500 Hz.

For eliminating the risk that the switch components of the switch means generate sparks and consequently cause a fire in case a combustible fluid, e.g. petrol, gasoline or diesel, is discharged from the atomizing nozzle device according to the present invention, an amplifier means may be provided, which amplifier means has a high input impedance and an output, the high impedance input is connected to the switch means for detecting the presence or the absence of the current path and the output being connected connector means of the electro-mechanical driver means. Consequently, the high input impedance of the amplifier means reduces the current of the current path, which is established and interrupted by the cooperating first and second switch components of the switch means, which high input impedance may reduce the current to such extremely low levels as a few micro-amperes or a few pico-amperes that the risk of generating fire the generation of sparks is eliminated.

The amplifier means may be constituted by e.g an FET transistor, an operational amplifier or any other appropriate high input impedance amplifier means.

In the above discussed preferred embodiment of the atomizing nozzle according to the present invention comprising a signal generator means, the amplifier means may further cooperate with the signal generator means for controlling the operation of the atomizing nozzle device. Thus, the amplifier means may receive the signal generated by the signal generator means and supply the signal generated by the signal generator means to the connector means, provided the current path is established, and interrupt the supply of the signal generated by the signal generator means to the connector means, provided the current path is interrupted. Obviously, in accordance with electronic techniques known in the art per se the signal generator means and the amplifier means may be operated in synchronism or be synchronized relative to one another in any appropriate manner and further, as discussed above, be enabled and controlled from an external source.

For providing a jet of droplets of a diameter of the order of 0.5–5 μm, the orifice has a diameter of the order of 0.1–3 mm, preferably 0.2–1 mm. For discharging a combustible fluid, such as petrol or gasoline, petrol drops of a diameter of 5 μm may be discharged from the atomizing nozzle device according to the present invention within a wide dynamic flow range of 30–650 ccm/min by means of an atomizing nozzle device having an orifice with a diameter within the above range. For a particular application field within the field of applying a nasal drug to a patient, extremely small drug doses, i.e. of the order of 5 ccm/sec, may be injected or discharged from the atomizing nozzle device in short pulses of a duration of 0.5 msec and having a diameter of the droplets of the jet of the order of 0.5–5 μm.

In accordance with this particular technical application of the present invention, an inhaler is provided comprising:

a housing having an outer wall defining an inner chamber of the housing, means for receiving a drug containing container and for introducing the drug into the chamber of the housing, said housing being provided with an orifice for discharging the fluid from the chamber a stem means comprising a closing element, the stem means being arranged within the housing so as to arrange the closing element juxtaposed the orifice for cooperating therewith, a spring means acting on the stem means for forcing the closing element thereof into the orifice for closing the orifice, an electro-mechanical driver means comprising a movable component and a stationary component, the movable component being connected to the stem means and the stationary component being connected to the housing, and the electro-mechanical drive means comprising connector means for receiving an electrical signal for causing the movable component to move relative to the stationary component and furthermore causing the closing element of the stem means to move relative to the orifice for opening the orifice, and a switch means including a first switch component and a second switch component, the first switch component being connected to the stem means and being movable therewith, the second switch component being connected to the stationary component, the first and second switch components being in contact with one another and establishing a current path to the connector means when the orifice is closed by the closing element, and the first and second switch components being out of contact with one another and interrupting the current path when the closing element is moved relative to the orifice.

The inhaler comprising an atomizing nozzle device according to the present invention may preferably be used for discharging a drug such as a nasal drug suspended in a liquid suspension, e.g, an aqueous suspension or a suspension of any other appropriate liquid or gas, which is inert or harmless to the patient.

An apparatus according to the invention in the form of an inhaler may be used for the administration of a drug or drugs to a patient. Drugs which may be relevant in this context are e.g. antiasthma drugs, antihistamines, expectorants, antitossives, antineoplastic agents active against lung tumors, antibiotics active against lung infections such as pneumonia, provided that the drug or drugs in question are dispersible in suitable form in a water based medium suitable for use in the inhaler according to the present invention.

Figure 2:
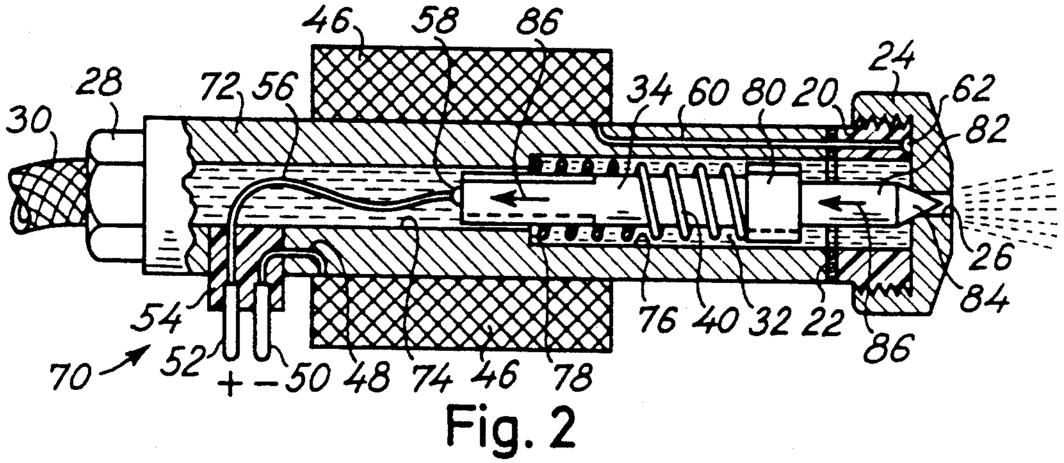
Figure 3:
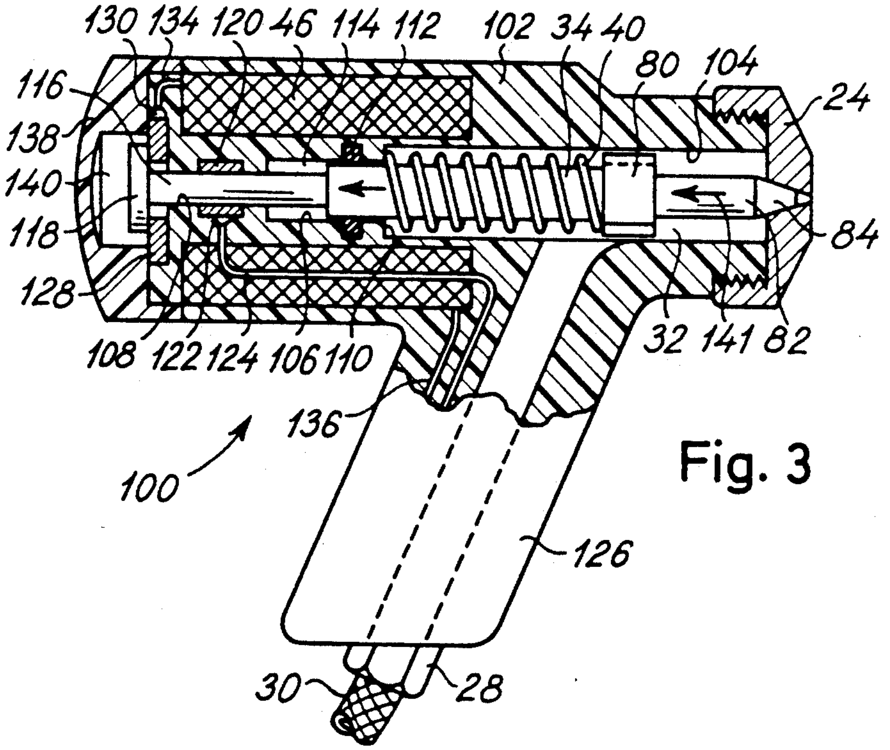
Figure 4:
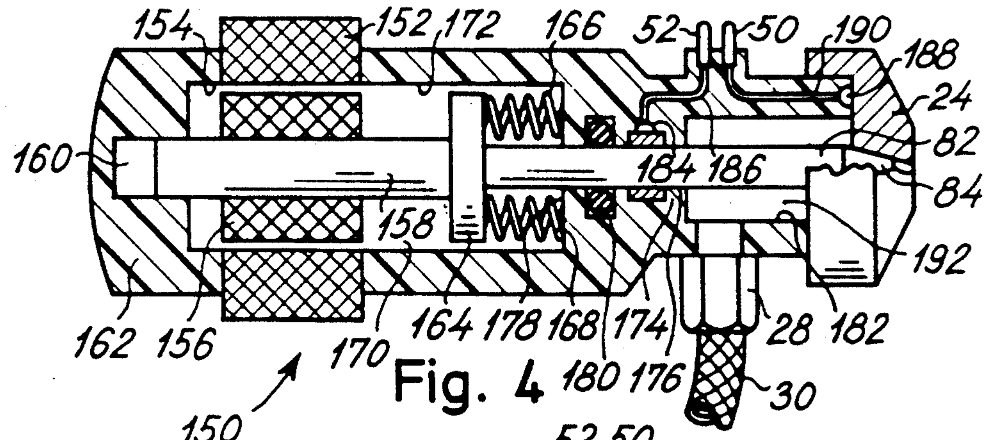
Figure 5:
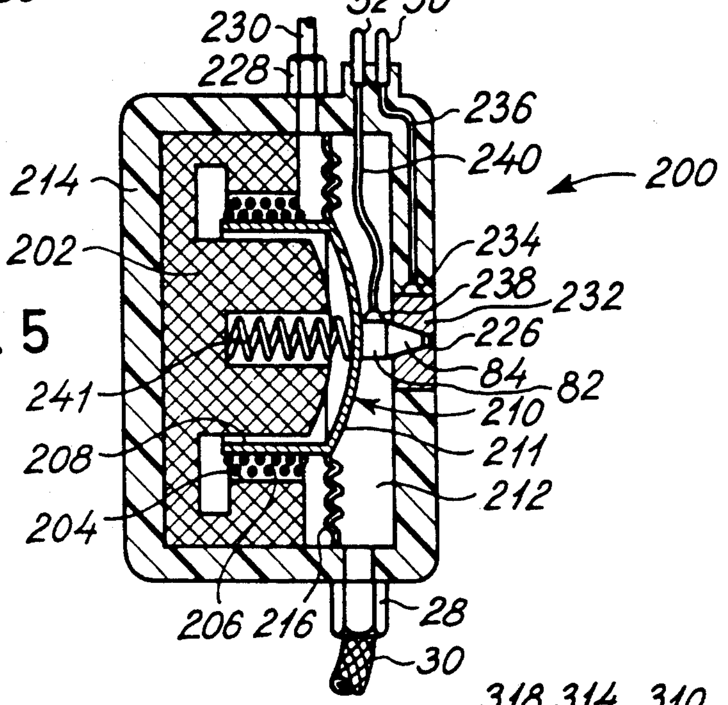
Figure 6:
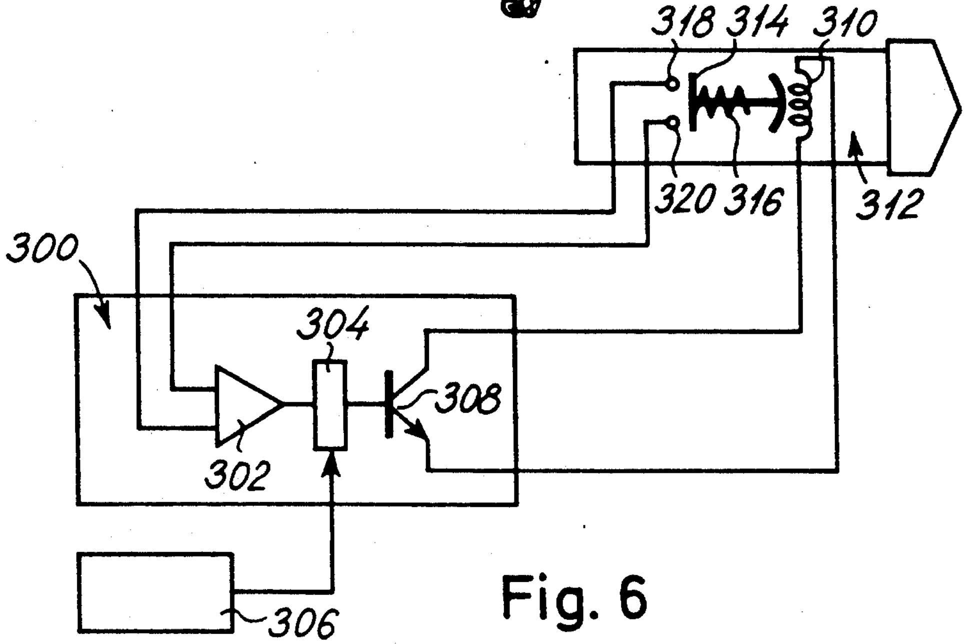
Figure 7:
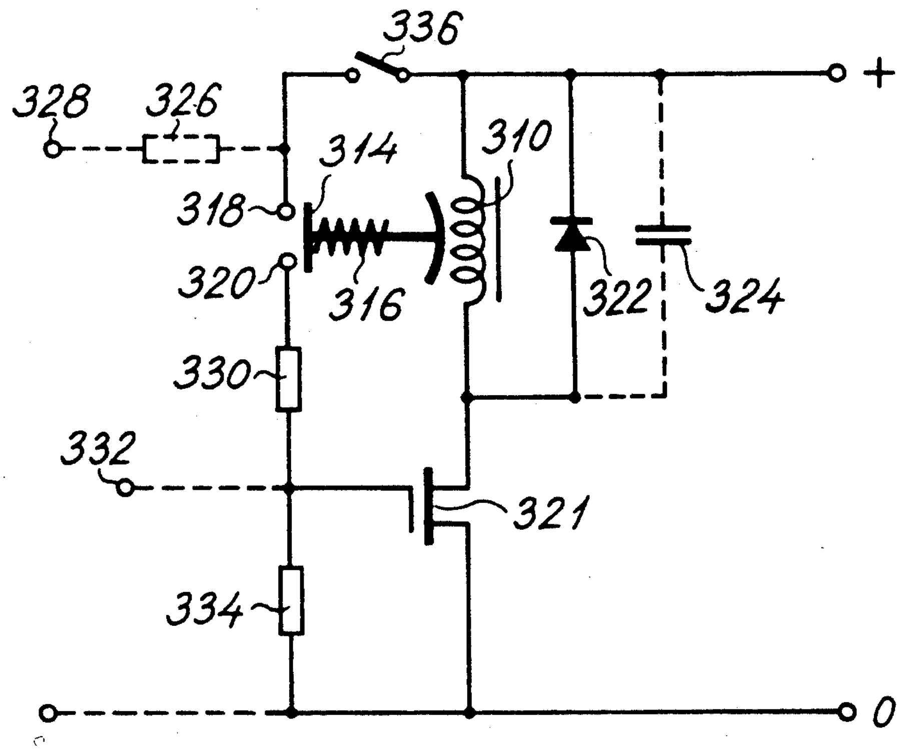
Figure 8:
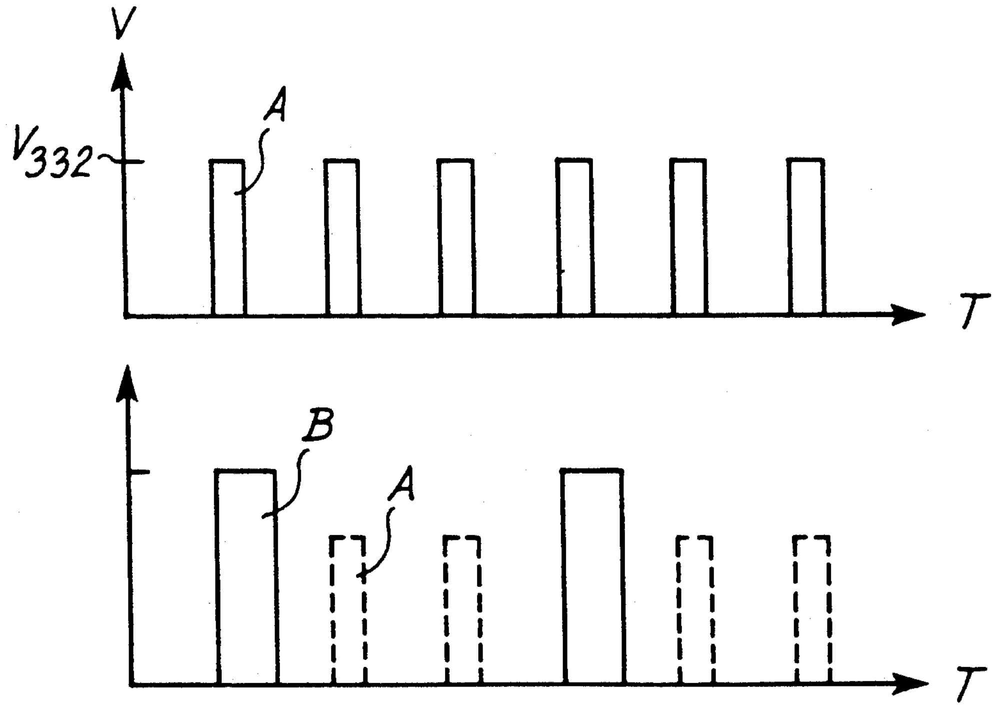
Figure 9:
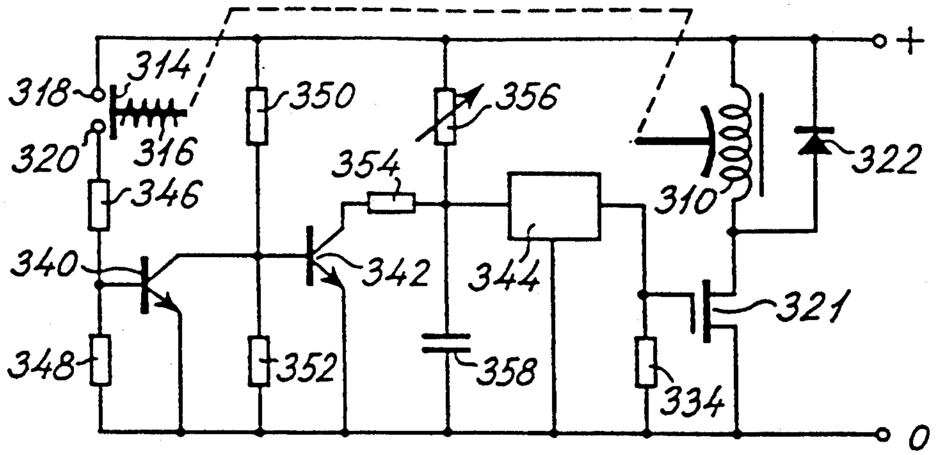
Figure 10:
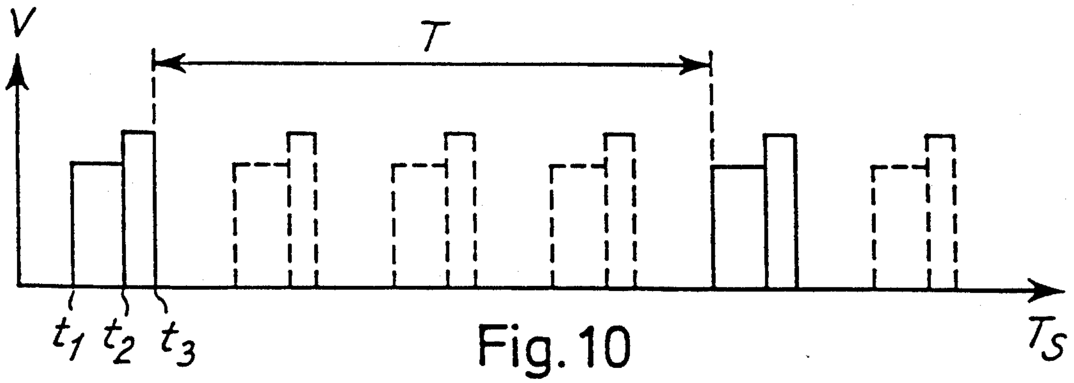
Figure 11:
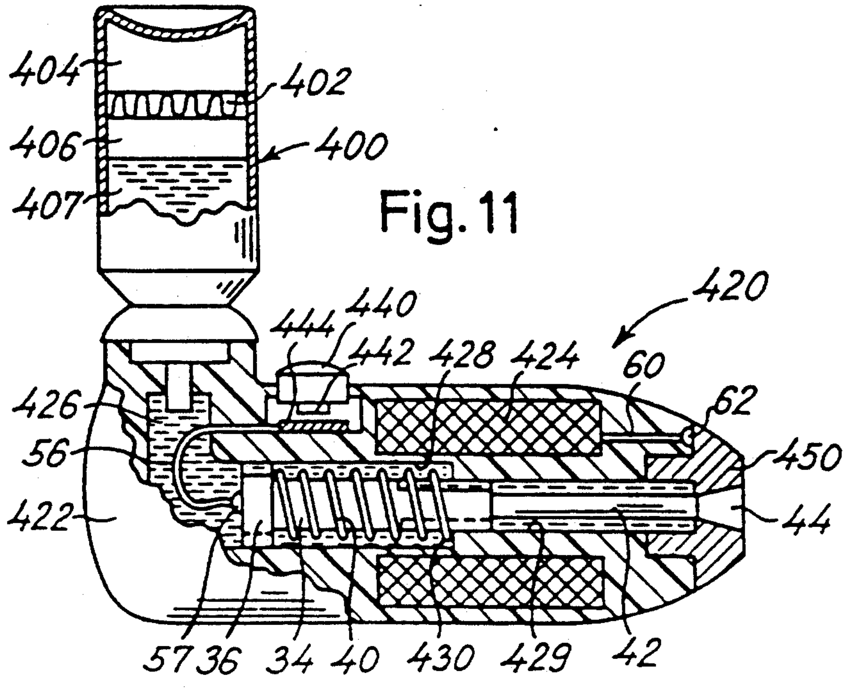

The invention will now be further described with reference to the drawings, in which FIGS. 1, 2 and 3 are schematic and sectional views of a first, a second and a third embodiment, respectively, of an atomizing nozzle device according to the present invention comprising a stationary coil and a movable armature, FIGS. 4 and 5 are sectional and schematic views of a fourth and a fifth embodiment, respectively, of an atomizing nozzle device according to the present invention implemented in accordance with an electro-dynamic principle, FIG. 6 is a block diagrammatical view of a control circuit of an atomizing nozzle device according to the present invention, FIG. 7 is a diagrammatical view of a control circuit for controlling the operation of an atomizing nozzle device according to the present invention, FIG. 8 is a diagrammatical view of control pulses generated by the control circuit shown in FIG. 7, FIG. 9 is a diagrammatical view of an alternative embodiment of a control circuit for controlling the operation of an atomizing nozzle device according to the present invention, FIG. 10 is a diagrammatical view of control pulses generated by the control circuit shown in FIG. 9, and FIG. 11 is a schematic and sectional view of an inhaler according to the present invention, including an atomizing nozzle device according to the present invention connected to a drug container.

In FIG. 1, a first embodiment of an atomizing nozzle device 10 according to the present is shown. The atomizing nozzle device comprises a circular cylindrical housing component 12 of a non-magnetic material, such as aluminum, brass, copper or, alternatively, a plastics material. Within the housing component 12, a cylindrical bore 14 of a first diameter and a cylindrical bore 16 of a second diameter are defined, which second diameter is larger than the first diameter. The cylindrical bores 14 and 16 define an annular surface 18. At the outer right-hand end of the housing component 12, an annular extension element 20 of a non-metallic or electrically insulating material is provided, which extension element 20 is glued to the housing component 12 through a glue layer 22. The annular extension element 20 is provided with an external thread, which cooperates with a meshing internal thread of a metallic screw cap 24. The metallic screw cap 24 is provided with a central aperture 26, which constitutes a discharge aperture or orifice of the atomizing nozzle device 10.

At the outer left-hand end of the housing component 12, a fitting 28 is provided for cooperating with a fluid supply hose 30, through which a fluid, such as a liquid, e.g. water, paint, glue, ink, gasoline, petrol, pure water or water containing a solid constituent, such as a drug, etc., or a gas, e.g. a pressurized gas, such a pressurized air, etc. is supplied. In FIG. 1, an inner space 32 defined within the atomizing nozzle device 10 by the bores 14 and 16 is illustrated filled with liquid as indicated by the signature. Within the space 32, a stem 34 is arranged, which stem is at its left-hand end provided with a disc shaped element 36. The stem 34 is as is evident from FIG. 1 provided with external longitudinal grooves for allowing that the liquid input to the atomizing nozzle device may pass the stem 34. Alternatively the stem 34 may be provided with one or more inner through-going bores, or further alternatively, the housing wall encircling the stem 34 may be provided with grooves serving the same purpose as the grooves of the stem 34. A coiled spring 40 encircles the stem 34 and cooperates with the disc shaped element 36 and the annular surface 18 so as to force the stem towards the outer left-hand end of the housing component 12. The stem 34 is at its right-hand end opposite to the disc shaped element 36 provided with a rod extension 42, which is further connected to a conical head 44, which cooperates with the aperture or orifice 26. As the conical head 44 tapers outwardly and as the force generated by the coiled spring 40 forces the conical head 44 into the aperture or orifice 26, the aperture or orifice 26 is consequently closed. Furthermore, discharge of fluid or liquid from the atomizing nozzle device 10 is prevented.

At the right-hand end of the housing component 12, a solenoid coil 46 is arranged encircling the housing component 12. The solenoid coil 46 is through a first wire 48 connected to a negative supply terminal 50, which is mounted within a terminal plug 54 of an insulated material together with a positive supply terminal 52. The positive supply terminal 52 is connected to the disc shaped element 36 through a wire 56 and a soldered connection 58. The disc shaped element 36 is of a metallic material, which is in direct electrically conductive contact with the stem 34, which is made of soft iron, and which is further connected in direct electrically conductive connection with the rod extension 42 and the conical head 44, which are also manufactured from metals, preferably metals of high electrical conductivities, such as aluminum, copper, brass stainless steel or the like, dependent on any particular requirements, e.g. resistance to the fluid or liquid, to which the metals of the elements are exposed. An opposite end of the solenoid coil 46 is connected to the metallic screw cap 24 through a wire 60 and a soldered connection 62.

The atomizing nozzle device 10 operates in the following manner. In its initial or rest position, the conical head 44 is, due to the force generated by the coiled spring 40, forced into the aperture or orifice 26 thereby closing the aperture or orifice and preventing any discharge of fluid or liquid from the atomizing nozzle device. The fluid or liquid is supplied to the atomizing nozzle device 10 through the hose 30 at a superatmospheric pressure level, which may vary within wide ranges without to any substantial extent influencing the movement of the stem 34 within the atomizing nozzle device 10, and further the size, i.e. the diameter, of the droplets of fluid discharged from the atomizing nozzle device. At a specific time, an energizing current, which may be a constant current, i.e. a current generated by a current source, or a current generated by the supply of a constant voltage from a voltage source, is supplied to the solenoid coil 46 through the terminals 50 and 52. As will be readily understood, a current path is established from the positive supply terminal 52 through the wire 56, the soldered connection 58, the disc shaped element 36, the stem 34, the rod extension 42, the head 44, the metallic screw cap 24, the soldered connection 62, the wire 60, the solenoid coil 46, and the wire 48 to the negative supply terminal 50. Consequently, the solenoid coil 46 generates a magnetic field within the chamber 32 and influences the stem 34 causing it to move to the right as indicated by arrows 64. As the stem 34 is moved to the right, the rod extension 42 and the head 44 are also moved to the right. Due to the conical shape of the head 44 the aperture or orifice 26 is consequently opened, so that fluid or liquid is discharged therefrom.

However, as the head 44 is moved to the right, the above current path from the positive supply terminal 52 to the negative supply terminal 50 is interrupted when the head 44 is brought out of electrically conductive contact with the metallic screw cap 24 resulting in that the current supplied to the solenoid coil 46 is interrupted. Consequently, the magnetic field generated by the solenoid coil 46 decreases with the effect in that the force generated by the coiled spring 40 forces the stem 34 and consequently the head 44 to the left so that the head 44 closes the opening or orifice 26 resulting in that the discharge of fluid of liquid from the aperture or orifice 26 is interrupted. However, at this state, the electrically conductive contact between the head 44 and the metallic screw cap 24 is reestablished, and the current path from the positive supply terminal 52 to the negative supply terminal 50 is consequently reestablished resulting in that the energizing current is supplied to the solenoid coil 46. The activation/de-activation of the coil continues until the current supplied to the terminals 52 and 50 is interrupted. As will be understood, the head 44 and the metallic screw cap 24 constitute a turn on/turn off switching means or element energizing and de-energizing the magnetic field generating coil 46 in accordance with a principle known per se from doorbells.

In FIG. 2 a slightly modified second embodiment of an atomizing nozzle device 70 according to the present invention is shown. The atomizing nozzle device 70 is of a structure very similar to that of the device 10 in FIG. 1, however different from the operational mode of the device 10 in that the stem 34 is forced to the right by the force generated by the coiled spring 40, as a housing component 72 of the atomizing nozzle device 70, which housing component corresponds to the housing component 12 of the atomizing nozzle device 10 shown in FIG. 1, is provided with a left-hand smaller diameter bore 74 and a right-hand larger diameter bore 76 between, which bores an annular surface 78, is provided, which annular surface corresponds to the annular surface 18 shown in FIG. 1 and against which annular surface 78 the coiled spring 40 rests. In the atomizing nozzle device 70, the disc shaped element 36 is omitted, and a disc shaped element 80 is provided at the right-hand end of the stem 34, which disc shaped element 80 is acted upon by the coiled spring 40. The disc shaped element 80 is in direct electrically conductive connection with the stem 34 and with a rod 82, which is provided with a pointed end 84. Provided no current is supplied to the solenoid coil 46, the pointed end 84 closes the aperture or orifice 26 preventing any fluid or liquid from discharging from the atomizing nozzle device 70. By the supply of an energizing current to the solenoid coil 46, the stem 34 is caused to move to the left as indicated by arrows 86, by which movement, the electrically conductive contact between the pointed end 84 and the metallic screw cap 24 is interrupted. As will be readily understood, the atomizing nozzle device 70 functions in a manner similar to that of the device 10 described in FIG. 1.

In FIG. 3, a slightly modified embodiment of the atomizing nozzle device 70 shown in FIG. 2 is shown. The atomizing nozzle devices 10 and 70 discussed above rely on an electrically conductive contact between on the one hand the head 44 and the pointed end 84 and on the other hand the metallic screw cap 24, which contact may for some applications be inadequate, as the cooperating elements on the one hand the head 44 and the pointed end 84 and on the other hand the metallic screw cap 24 may result in that electric sparks are generated, which for some applications, e.g. the discharging of combustible fluids or liquids, such as gasoline or the like, may cause a fire. For eliminating the risk of causing a fire, the contact elements establishing and interrupting the current path to the energizing coil of the atomizing nozzle device according to the present invention is in the embodiment shown in FIG. 3 shifted from the nozzle aperture or nozzle orifice to the opposite end of the device and further insulated relative to the fluid or liquid contained within the chamber 32. In the embodiment of the atomizing nozzle device 100 shown in FIG. 3, the solenoid coil 46 is cast into an insulating housing component 102, in which a first cylindrical bore 104 of a first diameter, a second cylindrical bore 106 of a second diameter, and a third cylindrical bore 108 of a third diameter, which bores 104, 106 and 108 are aligned coaxially. The first and second cylindrical bores 104 and 106 define an annular surface 110 corresponding to the annular surface 78 of the embodiment 70 shown in FIG. 2, against which annular surface 110 the coiled spring 40 rests. The second cylindrical bore 106 is provided with an annular groove, in which an O-ring 112 is received sealing against the outer circumferential surface of the stem 34 for preventing fluid or liquid contained within the chamber 32 from penetrating into a chamber 114 defined at the left-hand end of the second cylindrical bore 106. The stem 34 is at its left-hand end provided with a metallic rod 116, which is further provided with a head 118. The rod 116 extends through the third cylindrical bore 108 and cooperates with a journalling bearing 120, which is received within an annular groove of the third cylindrical bore 108 for establishing electrically conductive contact with the rod 116. The journalling bearing 120 is through a soldered joint 122 connected to a wire 124, which extends through the solenoid coil 46 and further into a handle part 126 of the housing component 102. At the left-hand end of the housing component 102, a ring element 128 is arranged recessed within the housing component 102 and cooperating with the head 118 in a manner similar to the switch elements of the above discussed embodiments 10 and 70 shown in FIGS. 1 and 2, respectively. The ring element 128 is through a soldered joint 130 connected to a wire 134, which is further connected to the solenoid coil 46. The opposite end of the solenoid coil 46 is connected to a wire 136, which extends into the handle part 126 together with the above discussed wire 124.

The left-hand end of the housing component 102 is encased within a cap 138, which is provided with a central aperture or recess 140, in which the head 118 is allowed to move. As will be readily understood, a current path is established from an external current supply through the wire 136, the solenoid coil 46, the wire 134, the soldered connection 130, the ring element 128, the head 118, the rod 116, the journalling bearing 120, the soldered connection 122 and the wire 124. The energizing current supplied to the solenoid coil 46 causes the stem 34 to move to the left as indicated by an arrow 141 and is in a manner similar to the above discussed manner interrupted by the switching elements 118 and 128.

In FIG. 4, a fourth embodiment of an atomizing nozzle device 150 according to the present invention is shown. Contrary to the above discussed first, second and third embodiments, which are implemented in accordance with an electro-magnetic principle, the atomizing nozzle device 150 is based on an electro-dynamic principle. Thus, the atomizing nozzle device 150 comprises a magnetic assembly 152, which defines a magnetic gap 154, in which a solenoid coil 156 is arranged. The wires establishing electrically conductive connection to the solenoid coil 156 are not shown in FIG. 4. The solenoid coil 156 is mounted on a stem 158, the left-hand end of which is received in a cylindrical bore 160 of a housing 162, which further supports the magnetic assembly 152. The right-hand end of the stem 158 is connected to a disc shaped element 164, which cooperates with two springs 166 and 168 forcing the disc shaped element to the right, as the springs 166 and 168 pull the disc shaped element 164 to the right. The stem 158, the disc shaped element 164 and the solenoid coil 156 are received within an inner space 170 defined within the housing 162, which inner space 170 is defined by a first cylindrical bore 172.

The housing component 162 is further provided with a central annular partition element 174, in which a second cylindrical bore 176 is defined, which second cylindrical bore 176 together with the first cylindrical bore 172 defines an annular surface 178, to which the pull springs 166 and 168 are fastened. In an annular groove of the second cylindrical bore 176, an O-ring 180 is arranged serving the same purpose as the O-ring 112 shown in FIG. 3. At the right-hand end of the housing component 162, a third cylindrical bore 182 is provided, into which the rod 82, also shown in FIG. 3, extends cooperating with the metallic screw cap 24, which is arranged at the utmost right-hand end of the housing component 162.

The rod 82 is through a soldered connection 184 and a wire 186 connected to the terminal 52, while the metallic screw cap 24 is connected through a soldered joint or connection 188 and a wire 190 to the terminal 50. As will be readily understood, the rod 82 and the metallic screw cap 24 shown in FIG. 4 serve the same purpose as the metallic rod 82 and the screw cap 24 shown in FIG. 2, i.e, of establishing and interrupting the current path to the solenoid coil 156, which current path is established through the terminals 50 and 52 and through the above-mentioned wires not shown in the drawings. The third cylindrical bore 182 defines a space 192, to which the fluid or liquid is supplied through a hole 144 and through the hose 30 and the fitting 28, also shown in FIGS. 1 and 2.

In FIG. 5, a fifth embodiment of an atomizing nozzle device 200 according to the present invention. The atomizing nozzle device 200 comprises centrally a magnetic assembly 202, which defines an annular magnetic gap 204, in which a coil 206 is arranged. The coil 206 is supported on a coil former 208, which coil former constitutes a part of a cup element 210 defining a domed membrane element 211. The coil 206 is insulated relative to the cup element 210. The cup element 210 is suspended within a space 212 defined within a housing component 214 by means of an annular suspension 216. The annular suspension 216 and the cup element 210 separate the inner space defined within the housing component 214 into two chambers, a front chamber into which fluid or liquid is supplied through a hose 30 and a fitting 28, and from which the fluid or liquid is discharged as a stream or jet of droplets from a discharge orifice 226 in accordance with the discharge technique of the present invention, and a rear chamber which may be pressurized by the supply of e.g pressurized air or pressurized magnetic fluid, such as magnetic oil, through a hose 230 and a fitting 228. The discharge orifice 226, which is defined in a metallic annular component 232, cooperates with the pointed end 84 of the rod 82, which is mechanically supported by the cup element 210, which is also of a metallic material. The annular metallic component 232 is connected through a soldered joint 234 and a wire 236 to the terminal 50, while the rod 82 is connected to the terminal 52 through a soldered connection 238 and a wire 240. As will be readily understood, the atomizing nozzle device shown in FIG. 5 is of a high efficiency structure similar to the structure known within the electro-dynamic field as a compression driver, which structure is controlled in its oscillation by the masses of the moving components exclusively, and independent of suspension stiffness, spring losses, etc. The inner surface of the cup element 210 is acted upon by a coiled spring 241, which forces the pointed end 84 of the rod into the aperture or orifice 226 of the annular metallic component 232 so as to establish a current path from the terminal 52 through the wire 240, the soldered connection 238, the cup element 210, the rod 82, the pointed end 84, the metallic annular component 232, the soldered connection 234, and the wire 236 to the terminal 50. Obviously, the discharging of fluid or liquid from the atomizing nozzle device 200 is established in a manner identical to the above discussed discharging technique.

It is however, to the emphasized that in accordance with the teachings of the present invention, the atomizing nozzle devices discussed above with reference to FIGS. 1-5 may be operated in an externally controlled oscillating mode by the supply of an oscillating signal to the solenoid coil of the atomizing nozzle devices instead of operating the atomizing nozzle devices in accordance with the autonomously oscillating principle in accordance with which the discharging of the fluid or liquid from the atomizing nozzle device is established by establishing and interrupting a current path to the solenoid coil of the atomizing nozzle device.

In FIG. 6 a block diagram of a control circuit for controlling the operation of the atomizing nozzle device according to the present invention is shown. The control circuit is enclosed within a solid line block 300 and comprises a high input impedance amplifier, such as an operational amplifier 302, a gate 304, which is enabled from an external enabling circuit 306 and an output current supplying element, such as an NPN transistor 308, which supplies current to a solenoid coil 310 of an atomizing nozzle device 312 shown schematically in FIG. 6. The atomizing nozzle device 312 may be implemented in accordance with any of the above discussed principles explained and discussed with reference to FIGS. 1-5 or any combination of these principles and further any other principles obvious to a person having ordinary skill in the art. The solenoid coil 310 causes in accordance with the teachings of the present invention a short-circuiting element 314 which is acted upon by a spring element 316, to establish and interrupt an electrically conductive connection between two terminals 318 and 320, which terminals are connected to the inputs of the high input impedance amplifier 302. By the provision of the high input impedance amplifier 302, the current supplied through the terminals 318 and 320 may constitute an extremely small current, such as a current of a few micro-ampere or pico-ampere.

In FIG. 7, a detailed diagram of a prototype implementation of the circuit shown in FIG. 6 is illustrated. In the prototype implementation of the electronic circuit, an FET transistor 321 was employed constituting the high input impedance amplifier element and current supplying transistor shown in FIG. 6. The FET transistor 321 is in a source grounded configuration and has its drain connected to a first terminal of the solenoid coil 310 and further to an anode of a protection diode 322 parallel with which a protection capacitor 324 may further be connected. The cathode of the diode 322 is connected to the second terminal of the solenoid coil 310 and further through a switch 336 to the terminal 318, which is further connected through a resistor 326 to an external terminal 328 to which an external synchronizing generator is connected.

The terminal 320 is connected to the gate of the FET transistor 321 through a high impedance resistor 330. The gate of the FET transistor 321 is further connected to an external terminal 332 and through a resistor 334 connected to the ground or the negative supply terminal O. In accordance with the teachings of the present invention, the solenoid coil 310 causes the short-circuiting element 314 to oscillate between a first state, in which the element 314 establishes a short-circuiting connection between the terminals 318 and 320 and consequently supplies current to the gate of the FET transistor 321 and a second state, in which the short-circuiting connection between the terminals 318 and 320 is interrupted, in which second state no current is supplied to the gate of the FET transistor 321, which is consequently turned off. Provided the switch 336 is in a short-circuiting state in which the positive supply is connected to the terminal 318, the electronic circuitry oscillates freely determined by the operation of the element 314 short-circuiting the terminals 318 and 320 and interrupting the short-circuiting connection between the terminals 318 and 320, as explained above. Provided the switch 336 is in the state shown in FIG. 7, in which the terminal 318 is connected to the terminal 328 through the resistor 326, exclusively, the oscillation of the electronic circuitry is synchronized by and controlled by the signal present at the terminal 328. Thus, provided a positive pulse is supplied to the terminal 328, the electronic circuitry is allowed to oscillate for a period of time determined by the duration of the pulse. After the terminal 318 has been shifted low, as the pulse previously supplied to the terminal 328 has shifted low, the oscillation of the electronic circuitry stops, and consequently any discharge from the atomizing nozzle device controlled by the electronic circuitry shown in FIG. 7 is blocked.

In FIG. 8, a diagram is shown illustrating pulses A generated at the gate of the FET transistor 321 representing the voltage $V_{332}$ of the terminal 332 as compared to the ground of the entire electronic circuitry.

Through the external terminal 328 and the resistor 326, pulses B shown in the lower part of FIG. 8 are supplied to the gate of the FET transistor 321 for synchronizing the atomizing nozzle device according to the present invention which is controlled by the electronic circuitry shown in FIG. 7, which pulses B supplied to the terminal 328 are shown in solid line in the lower part of FIG. 8, while the pulses A generated by the electronic circuitry shown in FIG. 7, when the electronic circuitry is allowed to freely oscillate, are shown in dotted line.

A further synchronizing refinement may be provided by employing an electronic circuitry shown in FIG. 9, in which the resistor 330 shown in FIG. 7 and interconnecting the terminal 320 and the gate of the FET transistor 321 is substituted by two emitter grounded transistor stages comprising a first transistor 340 and a second transistor 342 and further a Schmitt trigger 344. The transistor 340 is an NPN transistor, the base of which is connected to the terminal 320 through a resistor 346 and connected to the ground of the entire electronic circuitry through a resistor 348. The collector of the transistor 340 is connected to the base of the transistor 342, which is also an NPN transistor, the base of which is connected to the positive supply terminal through a resistor 350 and to the ground of the electronic circuitry through a resistor 352. The collector of the transistor 342 is connected to an input of the Schmitt trigger 344 through a resistor 354, which input is further connected through a variable resistor 356 to the positive supply and through a capacitor 358 to the ground of the entire electronic circuitry. By altering the resistance of the variable resistor 356, the charging of the capacitor 358 and consequently the delaying of the turning on of the field effect transistor 321 are controllable.

In FIG. 10, a diagram is shown, in which a span T illustrates the time constant of the RC network comprising the variable resistor 356 and the capacitor 358. At time $t_1$ the FET transistor 321 is turned on, and at time $t_2$ the atomizing nozzle device according to the present invention starts discharging fluid or liquid from its discharging aperture or orifice, at which time $t_2$ the short-circuiting connection between the terminals 318, 320 through the short-circuiting element 314 is interrupted. At time $t_3$, the discharging of fluid or liquid from the atomizing nozzle device controlled by the electronic circuitry shown in FIG. 9 is interrupted, and the short-circuiting element 314 reestablishes the short-circuiting connection between the terminals 318 and 320. The dotted line pulses shown in FIG. 10 illustrate the pulses generated within the electronic circuitry, provided the variable resistor 356 is omitted, resulting in a freely oscillating or free running operation of the electronic circuitry.

It is to be emphasized that by the provision of the FET transistor 321 shown in FIGS. 7 and 9 and further the high input impedance amplifier 302 shown in FIG. 6, the current supplied through the switching elements of the atomizing nozzle device according to the present invention is radically reduced to extremely small current levels, such as levels of micro-amperes or pico-amperes, making it perfectly safe to employ the atomizing nozzle device for expelling or discharging highly inflammable liquids, as e.g. gasoline or petrol. It is to be realised that by the switching element operation of the atomizing nozzle device according to the present invention, a perfectly metered charge of fluid or liquid is discharged from the atomizing nozzle device irrespective of the pressure prevailing within the atomizing nozzle device and any substantial fluctuations or changes of the pressure.

EXAMPLE 1

A prototype implementation of the atomizing nozzle device 10 shown in FIG. 1 was implemented from the following components:

The housing component 12 was made from PFTE/-POM and had an overall outer length of 45 mm The outer diameter of the housing component 12 was 10 mm, and the inner bores 14 and 16 of the housing component 12 were of diameters 3.5 mm and 6 mm respectively. The stem 34 was a cylindrical soft iron body of an outer diameter of 6 mm and a length of 25 mm. The rod extension 42 was an iron rod of an outer diameter of 1.5 mm and an inner diameter of 0.8 mm. The metal screw cap 24 was made from iron, in which a through-going aperture of a diameter of 1.2 mm was provided. The solenoid coil 46 was of a diameter of 30 mm, the wire of the solenoid coil was a Cu wire of a diameter of 0.2 mm, the total resistance of the solenoid coil was 30 Ω, and the axial length of the solenoid coil was 22 mm. The atomizing nozzle device was used for discharging water, oil and alcohol and was supplied with a DC voltage signal within the range of 12–24 V DC. The frequency of the discharging of the liquid from the atomizing nozzle device was 100–200 Hz dependent on the spring constant of the coiled spring 40 and the DC voltage supplied to the atomizing nozzle device. The on/off time period of the atomizing nozzle device was approx. 50%/50%. The atomizing nozzle device was also controlled by an electronic circuitry of the type shown in FIG. 7 as well as of the type shown in FIG. 9 (examples 3 and 4 respectively, below).

EXAMPLE 2

A prototype implementation of the atomizing nozzle device 130 shown in FIG. 2 was implemented from the following components:

The housing component 72 was made from PFTE/-POM and had an overall outer length of 60 mm. The outer diameter of the housing component was 8 mm, and the inner bores 74 and 76 of the housing component 12 were of diameters 5 mm and 6.5 mm, respectively. The stem 34 was a cylindrical soft iron body of an outer diameter of 6.5 mm and a length of 26 mm. The rod extension 86 was an iron rod of an outer diameter of 1.5 mm. The metal screw cap 24 was made from iron, in which a through-going aperture of a diameter of 1.0 mm was provided. The solenoid coil 46 was of a diameter of 30 mm, the wire of the solenoid coil was a 0.2 mm Cu wire, the total resistance of the solenoid coil was 30 Ω, and the axial length of the solenoid coil was 22 mm. The atomizing nozzle device was used for discharging water, oil and alcohol and was supplied with a DC voltage signal within the range of 12–24 V DC. The frequency of the discharging of the liquid from the atomizing nozzle device was 100–200 Hz dependent on the spring constant of the coiled spring 40 and the DC voltage supplied to the atomizing nozzle device.

EXAMPLE 3

The electronic circuitry shown in FIG. 7 was implemented from the following components:

The resistor 330 was a 47 kΩ resistor the resistor 334 was a 82 kΩ resistor, the FET transistor 321 was of the type 2N 665. The current supplied to the gate of the FET transistor 320 through the resistor 330 was between 180 μA and 500 μA, the current supplied to the solenoid coil 310 was approximately 1 A, and the positive supply voltage supplied through the switch 336 was +12 V.

EXAMPLE 4

The electronic circuitry shown in FIG. 9 was implemented from the following components:

The resistor 346 was a 10 kΩ resistor, the resistor 348 was a 47 kΩ resistor, the resistor 350 was a 4.7 kΩ resistor the resistor 352 was a 47 kΩ resistor, the resistor 354 was a 100 Ω resistor, the variable 356 was a 100 kΩ variable resistor the capacitor 358 was a 1 μF capacitor, the resistor 334 was a 10 kΩ resistor, the transistor 340 was a 2N 3904 NPN transistor, the transistor 342 was a 2N 3904 NPN transistor, the FET transistor 321 was a 2N 6659 FET transistor and the diode 322 was an 1N 4004 diode and the Schmitt trigger 344 was of the type 4093 supplied from the company RCA.

In FIG. 11, a special application of the atomizing nozzle device technique according to the present invention is shown, in accordance with which application the atomizing nozzle device is included in an inhaler for discharging a drug from a pressurized drug containing container 400. In the container 400, a miniature pressure regulator 402 separates an inner chamber defined within the container 400 into a space 404 with a pressurized gas atmosphere, such as an atmosphere of atmospheric air, carbon dioxide, $N_2$ or any other appropriate inactive gas of a pressure of e.g. 7 bar and a chamber 406 with a reduced pressure such as a pressure of 4 bar, and in which chamber an aqueous suspension 407 of a drug is included. The container 400 is provided with a ball valve closure mechanism for cooperating with an inhaler device according to the present invention, in which an atomizing nozzle device according to the present invention is included and of a structure identical to that shown in FIG. 1. The inhaler according to the present invention is designated the reference numeral 420 and comprises an outer housing 422, in which a solenoid coil 424 is enclosed. The housing component 422 further defines a first chamber 426, into which the aqueous solution or suspension is introduced from the container 400, and in which two cylindrical bores 428 and 429 are provided, which define an annular surface 430, with which the coiled spring 40 cooperates. The stem and the components connected thereto are identical to the components shown in FIG. 1 and are designated the same reference numerals. The inhaler 422 further includes a push button 440, which is provided with a metal bottom component 442 for establishing electrically conductive contact to a contact plate 444, to which the wire 56 is connected. By short-circuiting the metal bottom component 442 and the contact plate 444, a current path is established through the wire 56, the soldered connection 57, the disc shaped body 36, the stem 34, the rod extension 42, the conical head 44, a metallic end component 450 serving the same purpose as the metallic screw cap 24, the soldered connection 62, and the wire 60 to the solenoid coil 424 and from the solenoid coil 424 to a voltage supply, such as a battery supply, optionally an electronic circuitry of the type discussed above with reference to FIGS. 7 and 9, included within the inhaler 420, however, not shown on the drawing. The metal bottom component 442 and the contact plate 444 may constitute components connected to a timer circuit included within the inhaler, which timer circuit determines a period of time for which a specific dose is to be discharged from the inhaler, e.g. by generating a pulse, such as the pulse B shown in FIG. 8, which pulse B is supplied to the terminal 328 of the electronic circuitry shown in FIG. 7.

The inhaler shown in FIG. 11 may further be refined by the provision of an automatic turn on switch, which may comprise e.g. a reed contact, which is connected in parallel with or in substitution of the metal bottom component 442 and the contact plate 444 and is connected to the above described timer circuit, which reed contact is activated by a magnetic body, which is mounted on a small lever, which is caused to oscillate when the patient inhales through the inhaler, by which oscillation the magnetic body is moved past the read contact activating the reed contact and turning on the electronic circuitry for a period of time determined by the timer circuit. The timer circuit may, as is well known in the art, be implemented by e.g. an integrated electronic circuit of the type NE 555. Alternatively, the timer circuit may simply comprise a capacitor which is charged through a fairly low resistor and a diode and allowed to discharge through a fairly high resistor such as the series configuration of the resistor 326, 330, and 334 shown in FIG. 7.

By providing an atomizing nozzle device according to the present invention in an inhaler for discharging the drug extremely accurate amounts of drugs may be discharged to a patient receiving a jet of drug suspended in water droplets from the discharging orifice or aperture 26 of the device. Extremely small droplets of a diameter of 0.5 μm and of a maximum diameter of 5 μm are believed to be providable by an inhaler implemented in accordance with the above discussed technical solution, in which the discharging orifice or aperture is of the order of 0.1 mm–0.5 mm, such as of the order of 0.2 mm. By further synchronizing the discharging pulses in accordance with the above discussed technique, any accurately measured amount of drug may be discharged from the inhaler.

I claim:

1. An atomizing nozzle device for atomizing a fluid supplied thereto and comprising:

a housing having an outer wall defining an inner chamber of said housing, an inlet for introducing said fluid into said chamber, and an orifice for discharging said fluid from said chamber, a steam means comprising a closing element, saio stem means being arranged within said housing so as to arrange said closing element juxtaposed said orifice for cooperating therewith, a spring means acting on said stem means for forcing said closing element thereof into said orifice for closing said orifice, an electro-magnetic driver means comprising a magnetic assembly and coil, said magnetic assembly defining a magnetic gap in which said coil is arranged, said magnetic assembly constituting a stationary component, and said coil constituting a movable component, said movable component being connected to said stem means and said stationary component being connected to said housing, and said electro-mechanical drive means comprising connector means for receiving an electrical signal for causing said movable component to move relative to said stationary component and furthermore causing said closing element of said stem means to move relative to said orifice for opening said orifice, and a switch means including a first switch component and a second switch component, said first switch component being connected to said stem means and being movable therewith, said second switch component being connected to said stationary component, said first and second switch components being in contact with one another and establishing a current path to said connector means when said orifice is closed by said closing element, and said first and second switch components being out of contact with one another and interrupting said current path when said closing element is moved relative to said orifice.

2. An atomizing nozzle device according to claim 1, said closing element being made from a metallic material and said first switch component being constituted by said closing element, and said orifice being provided in a housing component of said housing, which housing component is made from a metallic component and constitutes said second switch component.

3. An atomizing nozzle device for atomizing a fluid supplied thereto and comprising:

a housing having an outer wall defining an inner chamber of said housing, an inlet for introducing said fluid into said chamber, and an orifice for discharging said fluid from said chamber, a stem means comprising a closing element, said stem means being arranged within said housing so as to arrange said closing element juxtaposed said orifice for cooperating therewith, a spring means acting on said stem means for forcing said closing element thereof into said orifice for closing said orifice, an electro-mechanical driver means being constituted by an electro-magnetic driver means comprising a magnetic assembly and coil, said magnetic assembly defining a magnetic gap in which said coil is arranged, said magnetic assembly constituting a movable component, and said coil constituting a stationary component, said movable component being connected to said stem means and said stationary component being connected to said housing, and said electro-mechanical drive means comprising connector means for receiving an electrical signal for causing said movable component to move relative to said stationary component and furthermore causing said closing element of said stem means to move relative to said orifice for opening said orifice, and a switch means including a first switch component and a second switch component, said first switch component being connected to said stem means and being movable therewith, said second switch component being connected to said stationary component, said first and second switch components being in contact with one another and establishing a current path to said connector means when said orifice is closed by said closing element, and said first and second switch components being out of contact with one another and interrupting said current path when said closing element is moved relative to said orifice.

4. An atomizing nozzle device according to claim 3 said closing element being made from a metallic material and said first switch component being constituted by said closing element, and said orifice being provided in a housing component of said housing, which housing component is made from a metallic component and constitutes said second switch component.

5. An atomizing nozzle device for atomizing a fluid supplied thereto and comprising:

a housing having an outer wall defining an inner chamber of said housing, an inlet for introducing said fluid into said chamber, and an orifice for discharging said fluid from said chamber, a steam means comprising a closing element, said stem means being arranged within said housing so as to arrange said closing element juxtaposed said orifice for cooperating therewith, a spring means acting on said stem means for forcing said closing element thereof into said orifice for closing said orifice, an electro-mechanical driver means comprising a movable component and a stationary component, said electro-mechanical driver means comprising a coil and an armature, said armature constituting said stationary component, and said coil constituting said movable component, said movable component being connected to said stem means and said stationary component being connected to said housing, and said electro-mechanical drive means comprising connector means for receiving an electrical signal for causing said movable component to move relative to said stationary component and furthermore causing said closing element of said stem means to move relative to said orifice for opening said orifice, and a switch means including a first switch component and a second switch component, said first switch component being connected to said stem means and being movable therewith, said second switch component being connected to said stationary component, said first and second switch components being in contact with one another and establishing a current path to said connector means when said orifice is closed by said closing element, and said first and second switch components being out of contact with one another and interrupting said current path when said closing element is moved relative to said orifice.

6. An atomizing nozzle device for atomizing a fluid supplied thereto and comprising:

a housing having an outer wall defining an inner chamber of said housing, an inlet for introducing said fluid into said chamber, and an orifice for discharging said fluid from said chamber, a stem means comprising a closing element, said stem means being arranged within said housing so as to arrange said closing element juxtaposed said orifice for cooperating therewith, a spring means acting on said stem means for forcing said closing element thereof into said orifice for closing said orifice, an electro-mechanical driver means comprising a movable component and a stationary component, said movable component being connected to said stem means and said stationary component being connected to said housing, and said electro-mechanical drive means comprising connector means for receiving an electrical signal for causing said movable component to move relative to said stationary component and furthermore causing said closing element of said stem means to move relative to said orifice for opening said orifice, a switch means including a first switch component and a second switch component, said first switch component being connected to said stem means and being movable therewith, said second switch component being connected to said stationary component, said first and second switch components being in contact with one another and establishing a current path to said connector means when said orifice is closed by said closing element, and said first and second switch components being out of contact with one another and interrupting said current path when said closing element is moved relative to said orifice, and an amplifier means having a high impedance input and an output, said high impedance input being connected to said switch means for detecting the presence and absence of said current path, and said output being connected to said connector means of said electro-mechanical driver means.

7. An atomizing nozzle device according to claim 6, said closing element being made from a metallic material and said first switch component being constituted by said closing element, and said orifice being provided in a housing component of said housing, which housing component is made from a metallic component and constitutes said second switch component.

8. An atomizing nozzle device according to claim 6, said amplifier means being constituted by an FET transistor.

9. An atomizing nozzle device according to claim 6, said amplifier means being constituted by an operational amplifier.

10. An atomizing nozzle device for atomizing a fluid supplied thereto and comprising:

a housing having an outer wall defining an inner chamber of said housing, an inlet for introducing said fluid into said chamber, and an orifice for discharging said fluid from said chamber, a stem means comprising a closing element, said stem means being arranged within said housing so as to arrange said closing element juxtaposed said orifice for cooperating therewith, a spring means acting on said stem means for forcing said closing element thereof into said orifice for closing said orifice, a signal generator means for generating an electrical signal, an electro-mechanical driver means comprising a movable component and a stationary component, said movable component being connected to said stem means and said stationary component being connected to said housing, and said electro-mechanical drive means comprising connector means for receiving an electrical signal for causing said movable component to move relative to said stationary component and furthermore causing said closing element of said stem means to move relative to said orifice for opening said orifice, a switch means including a first switch component and a second switch component, said first switch component being connected to said stem means and being movable therewith, said second switch component being connected to said stationary component, said first and second switch components being in contact with one another and establishing a current path to said connector means when said orifice is closed by said closing element, and said first and second switch components being out of contact with one another and interrupting said current path when said closing element is moved relative to said orifice, and an amplifier means having a high impedance input and an output, said high impedance input being connected to said switch means for detecting the presence and absence of said current path, and said output being connected to said connector means of said electro-mechanical driver means, said amplifier means further receiving said signal generated by said signal generator means and supplying said signal generated by said signal generator means to said connector means, provided said current path is established, and interrupting the supply of said signal generated by said signal generator means to said connector means provided said current path is interrupted.

11. An atomizing nozzle device according to claim 10, said closing element being made from a metallic material and said first switch component being constituted by said closing element, and said orifice being provided in a housing component of said housing, which housing component is made from a metallic component and constitutes said second switch component.

12. An inhaler for atomizing a drug supplied thereto and comprising:

a housing having an outer wall defining an inner chamber of said housing, and an orifice for discharging said drug from said chamber, means for receiving a drug containing container and for introducing said drug into said chamber of said housing, a stem means comprising a closing element, said stem means being arranged within said housing so as to arrange said closing element juxtaposed said orifice for cooperating therewith, a spring means acting on said stem means for forcing said closing element thereof into said orifice for closing said orifice, an electro-mechanical driver means comprising a movable component and a stationary component, said movable component being connected to said stem means and said stationary component being connected to said housing, and said electro-mechanical drive means comprising connector means for receiving an electrical signal for causing said movable component to move relative to said stationary component and furthermore causing said closing element of said stem means to move relative to said orifice for opening said orifice, and a switch means including a first switch component and a second switch component, said first switch component being connected to said stem means and being movable therewith, said second switch component being connected to said stationary component, said first and second switch components being in contact with one another and establishing a current path to said connector means when said orifice is closed by said closing element, and said first and second switch components being out of contact with one another and interrupting said current path when said closing element is moved relative to said orifice.

13. An inhaler for atomizing a drug supplied thereto and comprising:

a housing having an outer wall defining an inner chamber of said housing, and an orifice for discharging said drug from said chamber, said housing comprising a metallic housing component in which housing component said orifice is provided, means for receiving a drug containing container and for introducing said drug into said chamber of said housing, a stem means comprising a closing element, said stem means being arranged within said housing so as to arrange said closing element juxtaposed said orifice for cooperating therewith, said closing element being made from a metallic material, a spring means acting on said stem means for forcing said closing element thereof into said orifice for closing said orifice, an electro-mechanical driver means comprising a movable component and a stationary component, said movable component being connected to said stem means and said stationary component being connected to said housing, and said electro-mechanical drive means comprising connector means for receiving an electrical signal for causing said movable component to move relative to said stationary component and furthermore causing said closing element of said stem means to move relative to said orifice for opening said orifice, and a switch means including a first switch component and a second switch component, said first switch component being constituted by said closing element, said second switch component being constituted by said metallic housing component, said first and second switch components being in contact with one another and establishing a current path to said connector means when said orifice is closed by said closing element, and said first and second switch components being out of contact with one another and interrupting said current path when said closing element is moved relative to said orifice.

14. An inhaler for atomizing a drug supplied thereto and comprising:

a housing having an outer wall defining an inner chamber of said housing, and an orifice for discharging said drug from said chamber, means for receiving a drug containing container and for introducing said drug into said chamber of said housing, a stem means comprising a closing element, said stem means being arranged within said housing so as to arrange said closing element juxtaposed said orifice for cooperating therewith, a spring means acting on said stem means for forcing said closing element thereof into said orifice for closing said orifice, an electro-magnetic-driver means comprising a magnetic assembly and coil, said magnetic assembly defining a magnetic gap in which said coil is arranged, said magnetic assembly constituting a stationary component, and said coil constituting a movable component, said movable component being connected to said stem means and said stationary component being connected to said housing, and said electro-mechanical drive means comprising connector means for receiving an electrical signal for causing said movable component to move relative to said stationary component and furthermore causing said closing element of said stem means to move relative to said orifice for opening said orifice, and a switch means including a first switch component and a second switch component, said first switch component being connected to said stem means and being movable therewith, said second switch component being connected to said stationary component, said first and second switch components being in contact with one another and establishing a current path to said connector means when said orifice is closed by said closing element, and said first and second switch components being out of contact with one another and interrupting said current path when said closing element is moved relative to said orifice.

15. An inhaler according to claim 14, said closing element being made from a metallic material and said first switch component being constituted by said closing element, and said orifice being provided in a housing component of said housing, which housing component is made from a metallic component and constitutes said second switch component.

16. An inhaler for atomizing a drug supplied thereto and comprising:

a housing having an outer wall defining an inner chamber of said housing, and an orifice for discharging said drug from said chamber, means for receiving a drug containing container and for introducing said drug into said chamber of said housing, a stem means comprising a closing element, said stem means being arranged within said housing so as to arrange said closing element juxtaposed said orifice for cooperating therewith, a spring means acting on said stem means for forcing said closing element thereof into said orifice for closing said orifice, an electro-mechanical driver means being constituted by an electro-magnetic driver means comprising a magnetic assembly and coil, said magnetic assembly defining a magnetic gap in which said coil is arranged, said magnetic assembly constituting a movable component, and said coil constituting a stationary component, said movable component being connected to said stem means and said stationary component being connected to said housing, and said electro-mechanical drive means comprising connector means for receiving an electrical signal for causing said movable component to move relative to said stationary component and furthermore causing said closing element of said stem means to move relative to said orifice for opening said orifice, and a switch means including a first switch component and a second switch component, said first switch component being connected to said stem means and being movable therewith, said second switch component being connected to said stationary component, said first and second switch components being in contact with one another and establishing a current path to said connector means when said orifice is closed by said closing element, and said first and second switch components being out of contact with one another and interrupting said current path when said closing element is moved relative to said orifice.

17. An inhaler according to claim 16, said closing element being made from a metallic material and said first switch component being constituted by said closing element, and said orifice being provided in a housing component of said housing, which housing component is made from a metallic component and constitutes said second switch component.

18. An inhaler for atomizing a drug supplied thereto and comprising:

a housing having an outer wall defining an inner chamber of said housing, and an orifice for discharging said drug from said chamber, means for receiving a drug containing container and for introducing said drug into said chamber of said housing, a stem means comprising a closing element, said stem means being arranged within said housing so as to arrange said closing element juxtaposed said orifice for cooperating therewith, a spring means acting on stem means for forcing said closing element thereof into said orifice for closing said orifice, an electro-mechanical driver means comprising a movable component and a stationary component, said electro-mechanical driver means comprising a coil and an armature, said armature constituting said stationary component, and said coil constituting said movable component, said movable component being connected to said stem means and said stationary component being connected to said housing, and said electro-mechanical drive means comprising connector means for receiving an electrical signal for causing said movable component to move relative to said stationary component and furthermore causing said closing element of said stem means to move relative to said orifice for opening said orifice, and a switch means including a first switch component and a second switch component, said first switch component being connected to said stem means and being movable therewith, said second switch component being connected to said stationary component, said first and second switch components being in contact with one another and establishing a current path to said connector means when said orifice is closed by said closing element, and said first and second switch components being out of contact with one another and interrupting said current path when said closing element is moved relative to said orifice.

19. An inhaler according to claim 18, said closing element being made from a metallic material and said first switch component being constituted by said closing element, and said orifice being provided in a housing component of said housing, which housing component is made from a metallic component and constitutes said second switch component.

20. An inhaler for atomizing a drug supplied thereto and comprising:

a housing having an outer wall defining an inner chamber of said housing, and an orifice for discharging said drug from said chamber, means for receiving a drug containing container and for introducing said drug into said chamber of said housing, a stem means comprising a closing element, said stem means being arranged within said housing so as to arrange said closing element juxtaposed said orifice for cooperating therewith, a spring means acting on said stem means for forcing said closing element thereof into said orifice for closing said orifice, an electro-mechanical driver means comprising a movable component and a stationary component, said electro-mechanical driver means comprising a coil and an armature, said coil constituting said stationary component, and said armature constituting said movable component, said movable component being connected to said stem means and said stationary component being connected to said housing, and said electro-mechanical drive means comprising connector means for receiving an electrical signal for causing said movable component to move relative to said stationary component and furthermore causing said closing element of said stem means to move relative to said orifice for opening said orifice, and a switch means including a first switch component and a second switch component, said first switch component being connected to said stem means and being movable therewith, said second switch component being connected to said stationary component, said first and second switch components being in contact with one another and establishing a current path to said connector means when said orifice is closed by said closing element, and said first and second switch components being out of contact with one another and interrupting said current path when said closing element is moved relative to said orifice.

21. An inhaler according to claim 20, said closing element being made from a metallic material and said first switch component being constituted by said closing element, and said orifice being provided in a housing component of said housing, which housing component is made from a metallic component and constitutes said second switch component.

22. An inhaler according to claim 20, said armature being constituted by an iron component of said stem means.

23. An inhaler for atomizing a drug supplied thereto and comprising:

a housing having an outer wall defining an inner chamber of said housing, and an orifice for discharging said drug from said chamber, means for receiving a drug containing container and for introducing said drug into said chamber of said housing, a stem means comprising a closing element, said stem means being arranged within said housing so as to arrange said closing element juxtaposed said orifice for cooperating therewith, a spring means acting on said stem means for forcing said closing element thereof into said orifice for closing said orifice, a signal generator means for generating an electrical signal, said electrical signal chosen from the group consisting of an AC signal, a DC signal, and a combination of an AC and DC signal, an electro-mechanical driver means comprising a movable component and a stationary component, said movable component being connected to said stem means and said stationary component being connected to said housing, and said electro-mechanical drive means comprising connector means for receiving said electrical signal for causing said movable component to move relative to said stationary component and furthermore causing said closing element of said stem means to move relative to said orifice for opening said orifice, and a switch means including a first switch component and a second switch component, said first switch component being connected to said stem means and being movable therewith, said second switch component being connected to said stationary component, said first and second switch components being in contact with one another and establishing a current path to said connector means when said orifice is closed by said closing element, and said first and second switch components being out of contact with one another and interrupting said current path when said closing element is moved relative to said orifice.

24. An inhaler according to claim 23, said closing element being made from a metallic material and said first switch component being constituted by said closing element, and said orifice being provided in a housing component of said housing, which housing component is made from a metallic component and constitutes said second switch component.

25. An inhaler according to claim 23, said electrical signal generated by said signal generator means being an AC signal, said AC signal being chosen from the group consisting of a sinusoidal signal, a square wave signal, and a triangularly shaped signal.

26. An inhaler for atomizing a drug supplied thereto and comprising:

a housing having an outer wall defining an inner chamber of said housing, and an orifice for discharging said drug from said chamber, means for receiving a drug containing container and for introducing said drug into said chamber of said housing, a stem means comprising a closing element, said stem means being arranged within said housing so as to arrange said closing element juxtaposed said orifice for cooperating therewith, a spring means acting on said stem means for forcing said closing element thereof into said orifice for closing said orifice, an electro-mechanical driver means comprising a movable component and a stationary component, said movable component being connected to said stem means and said stationary component being connected to said housing, and said electro-mechanical drive means comprising connector means for receiving an electrical signal for causing said movable component to move relative to said stationary component and furthermore causing said closing element of said stem means to move relative to said orifice for opening said orifice, a switch means including a first switch component and a second switch component, said first switch component being connected to said stem means and being movable therewith, said second switch component being connected to said stationary component, said first and second switch components being in contact with one another and establishing a current path to said connector means when said orifice is closed by said closing element, and said first and second switch components being out of contact with one another and interrupting said current path when said closing element is moved relative to said orifice, and an amplifier means having a high impedance input and an output, said high impedance input being connected to said switch means for detecting the presence and absence of said current path, and said output being connected to said connector means of said electro-mechanical driver means.

27. An inhaler according to claim 26, said closing element being made from a metallic material and said first switch component being constituted by said closing element, and said orifice being provided in a housing component of said housing, which housing component is made from a metallic component and constitutes said second switch component.

28. An inhaler according to claim 26, said amplifier means being constituted by an FET transistor.

29. An inhaler according to claim 26, said amplifier means being constituted by an operational amplifier.

30. An inhaler for atomizing a drug supplied thereto and comprising:

a housing having an outer wall defining an inner chamber of said housing, and an orifice for discharging said drug from said chamber, means for receiving a drug containing container and for introducing said drug into said chamber of said housing, a stem means comprising a closing element, said stem means being arranged within said housing so as to arrange said closing element juxtaposed said orifice for cooperating therewith, a spring means acting on said stem means for forcing said closing element thereof into said orifice for closing said orifice, a signal generator means for generating an electrical signal, an electro-mechanical driver means comprising a movable component and a stationary component, said movable component being connected to said stem means and said stationary component being connected to said housing, and said electro-mechanical drive means comprising connector means for receiving an electrical signal for causing said movable component to move relative to said stationary component and furthermore causing said closing element of said stem means to move relative to said orifice for opening said orifice, a switch means including a first switch component and a second switch component, said first switch component being connected to said stem means and being movable therewith, said second switch component being connected to said stationary component, said first and second switch components being in contact with one another and establishing a current path to said connector means when said orifice is closed by said closing element, and said first and second switch components being out of contact with one another and interrupting said current path when said closing element is moved relative to said orifice, and an amplifier means having a high impedance input and an output, said high impedance input being connected to said switch means for detecting the presence and absence of said current path, and said output being connected to said connector means of said electro-mechanical drive means, said amplifier means further receiving said signal generated by said signal generator means and supplying said signal generated by said signal generator means to said connector means, provided said current path is established, and interrupting the supply of said signal generated by said signal generator means to said connector means provided said current path is interrupted.

31. An inhaler according to claim 30, said closing element being made from a metallic material and said first switch component being constituted by said closing element, and said orifice being provided in a housing component of said housing, which housing component is made from a metallic component and constitutes said second switch component.

32. An inhaler for atomizing a drug supplied thereto and comprising:

a housing having an outer wall defining an inner chamber of said housing, and an orifice for discharging said drug from said chamber, said orifice having a diameter of the order of 0.1–3 mm, means for receiving a drug containing container and for introducing said drug into said chamber of said housing, a stem means comprising a closing element, said stem means being arranged within said housing so as to arrange said closing element juxtaposed said orifice for cooperating therewith, a spring means acting on said stem means for forcing said closing element thereof into said orifice for closing said orifice, an electro-mechanical drive means comprising a movable component and a stationary component, said movable component being connected to said stem means and said stationary component being connected to said housing, and said electro-mechanical drive means comprising connector means for receiving an electrical signal for causing said movable component to move relative to said stationary component and furthermore causing said closing element of said stem means to move relative to said orifice for opening said orifice, and a switch means including a first switch component and a second switch component, said first switch component being connected to said stem means and being movable therewith, said second switch component being connected to said stationary component, said first and second switch components being in contact with one another and establishing a current path to said connector means when said orifice is closed by said closing element, and said first and second switch components being out of contact with one another and interrupting said current path when said closing element is moved relative to said orifice.

33. An inhaler according to claim 32, said closing element being made from a metallic material and said first switch component being constituted by said closing element, and said orifice being provided in a housing component of said housing, which housing component is made from a metallic component and constitutes said second switch component.

34. An atomizing nozzle device for atomizing a fluid supplied thereto, comprising:

a housing having an outer wall defining an inner chamber of said housing, an inlet for introducing said fluid into said inner chamber and an orifice for discharging said fluid from said inner chamber, said housing comprising a metallic housing component, said metallic housing component including said orifice;

stem means comprising a closing element, said stem means being arranged within said housing so as to arrange said closing element juxtaposed said orifice for cooperating therewith, said closing element being made from a metallic material;

spring means acting on said stem means for forcing said closing element into said orifice to close said orifice;

electro-mechanical driver means comprising a movable component and a stationary component, said movable component being connected to said stem means and said stationary component being connected to said housing, said electro-mechanical driver means further comprising connector means for receiving an electrical signal for causing said movable component to move relative to said stationary component and furthermore causing said closing element of said stem means to move relative to said orifice for opening said orifice; and switch means comprising a first switch component and a second switch component, said first switch component being constituted by said closing element, said second switch component being constituted by said metallic housing component, said first and second switch components being in contact with one another and establishing a current path to said connector means when said orifice is closed by said closing element, and said first and second switch components being out of contact with one another and interrupting said current path when said closing element is moved relative to said orifice.

* * * * *